United States Patent
Blumberg

(10) Patent No.: US 6,634,211 B1
(45) Date of Patent: Oct. 21, 2003

(54) METHOD TRANSLATION IN GAS CHROMATOGRAPHY

(76) Inventor: Leonid M. Blumberg, 6 Victoria Ct., Hockessin, DE (US) 19707

( * ) Notice: Subject to any disclaimer, the term of this patent is extended or adjusted under 35 U.S.C. 154(b) by 0 days.

(21) Appl. No.: 10/147,955

(22) Filed: May 16, 2002

Related U.S. Application Data

(60) Provisional application No. 60/291,406, filed on May 16, 2001.

(51) Int. Cl.[7] .................. G01N 30/02; B01D 15/08; G06F 17/10
(52) U.S. Cl. .................. 73/23.36; 210/659; 703/2
(58) Field of Search ............... 73/23.36, 23.35, 73/23.22, 23.27, 23.42; 210/198.2, 656, 659, 89; 703/2

(56) References Cited

U.S. PATENT DOCUMENTS

| | | | |
|---|---|---|---|
| 4,422,942 A | * 12/1983 | Allington | 210/659 |
| 4,962,662 A | * 10/1990 | Berger | 73/23.42 |
| 5,163,979 A | * 11/1992 | Patrick et al. | 95/19 |
| 5,405,432 A | 4/1995 | Snyder et al. | 95/82 |
| 5,611,846 A | * 3/1997 | Overton et al. | 96/102 |
| 5,827,946 A | 10/1998 | Klee et al. | 73/23.36 |
| 5,859,360 A | * 1/1999 | Magni et al. | 73/19.05 |
| 5,987,959 A | 11/1999 | Klee et al. | 73/1.02 |
| 6,036,747 A | 3/2000 | Blumberg et al. | 95/82 |
| 6,153,438 A | 11/2000 | Blumberg et al. | 436/161 |
| 6,494,078 B1 | * 12/2002 | Klee | 73/23.35 |
| 2002/0010566 A1 | * 1/2002 | Chester et al. | 703/2 |

FOREIGN PATENT DOCUMENTS

EP  0 570 707 B1  11/1993

OTHER PUBLICATIONS

Snyder, W.D. et al., "Constant Peak Elution Temperature with GC Columns of Different Diameter. How to Increase Analysis Speed with Little or no Less in Resolution", *Proceedings of 14th International Symposium on Capillary Chromatography*, Baltimore, May 25, 1992–May 29, 1992, ISCC92, Baltimore, 1992, Sandra, P. Editor; 28–38.

Blumberg, L.M. et al., "Method Translation and Retention Time Locking in Partition GC", *Anal. Chem,* 1998, 70(18), 3828–3839.

"GC Capillary Column Method Translation Software", *GC Method Translation Software,* A Product of Agilent Technologies, Inc. Wilmington, DE. www.agilent.com, 1 page.

"Lock in the Power of Gas Chromatography. Its Time", *Retention Time Locking Software,* Product G2080AA; Agilent Technologies, Inc. Wilmington, DE, 5 pages.

Quimby, B.D. et al., "Speed Improvement in Detailed Hydrocarbon Analysis of Gasoline Using 100–um Capillary Columns", 1995, Application Note 228–294, Hewlett–Packard Co., Wilmington, DE.

Klee, M.S. et al., "Predictable Translation of Capillary Gas Chromatography Methods for Fast GC", 1997, Application Note 228–373, Hewlett–Packard Co; Wilmington DE.

Klee, M.S. et al., "Theoretical and Practical Aspects of Fast Gas Chromatography and Method Translation", *J. Chromatogr. Sci,* 2002, 40, 234.

* cited by examiner

Primary Examiner—Hezron Williams
(74) Attorney, Agent, or Firm—James K. Luchs

(57) ABSTRACT

A method is provided for translating from a first method for performing gas chromatographic analysis to a second method for performing gas chromatographic analysis in a gas chromatography system without changing a peak elution pattern. Unlike the known method translation techniques that work only with the constant pressure gas chromatographic analyses, the invention can translate the gas chromatographic methods where column pressure and/or carrier gas flow rate change during the analysis by an arbitrary program.

16 Claims, No Drawings

METHOD TRANSLATION IN GAS CHROMATOGRAPHY

CROSS REFERENCE TO RELATED APPLICATIONS

This application claims benefit of Provisional Application No 60/291,406, filed May 16, 2001, the entirety of which is incorporated herein by reference.

FIELD OF THE INVENTION

The present invention relates to gas chromatography (GC). More particularly, the present invention relates to method translation, method development automation, method optimization, solute identification, improving reproducibility of elution pattern (elution pattern locking), method porting, and the like.

BACKGROUND OF THE INVENTION

Gas Chromatography

A typical gas chromatography (GC) system is comprised of a gas chromatograph and a computer controller as described in U.S. Pat. No. 5,405,432. The prime task of a chromatographic analysis of a sample mixture of chemical compounds (also known as analytes or solutes) by a GC system is to separate the solutes from each other, to identify them, and to quantify their amounts.

The separation of individual solutes in a sample mixture takes place in a chromatographic column also described in U.S. Pat. No. 5,405,432. Due to the different interaction of different solutes with the stationary phase in the column, it takes a different amount of time for the different solutes to travel through the column. As a result, the solutes, simultaneously injected in the column as a single mixture, elute from the column at different times, thus causing the separation of the solutes from each other. A detector converts the sequence of the solutes eluting from the column into a chromatogram—a sequence of chromatographic peaks—that can be electronically stored in a computer memory and/or displayed (e.g., electronically, on paper, etc.). Several examples of chromatograms are shown in U.S. Pat. No. 5,405,432.

The identity of each analyte, separated by the column, is typically associated with retention time (also known as elution time), $t_R$, of the corresponding peak in a chromatogram. A typical computer aided identification of the separated solutes makes use of a calibration table—an electronic list of records for all solutes of interest. Each record contains a solute identification and a retention time of the corresponding peak for that solute. A calibration table may also include information regarding tolerance windows for the retention times, as well as other information. A solute of interest can be correctly identified if its actual retention time in a particular analysis falls within the tolerance window for its retention time. To prevent a misidentification of a given peak with its immediately preceding or a following neighbor, the tolerance windows must have relatively narrow widths. This, in turn, may require a relatively high reproducibility of retention times for all peaks.

As described in U.S. Pat. No. 5,405,432, a solute's retention time depends on many parameters such as the column length, L, internal diameter, $d_c$, stationary phase film thickness, $d_f$, stationary phase type, carrier gas type, column pressure, column flow rate, and column temperature, T. Some of these parameters, such as the gas pressure or flow rate and the column temperature, can either remain constant during a given analysis or can change according to predetermined programs. The column parameters together with the calibration table and with the parameters of other components (injectors, detectors, etc.) of a GC system comprise a particular method of analysis of a particular mixture. Any change in the relevant method parameters can lead to the change in the retention times of some or all peaks. If the retention time changes are not accompanied by the necessary changes in the calibration table, misidentification of some or all solutes can occur.

Generally, it is difficult to predict the retention time changes caused by arbitrary changes in the method parameters. However, there are practically important exceptions. A concept of void time, $t_M$, is useful for the description of these exceptions. The void time is a retention time of a so-called unretained solute—that is, one that does not interact with the stationary phase, and, as a result, travels with the same velocity as the velocity of a carrier gas. Methane is frequently used as an unretained solute in practical measurements of $t_M$.

Method Translation

In some cases, the changes to retention times caused by a change in a method parameter can be predicted. The first case is referred to as method translation and may be applied to methods employing a constant pressure, as well as some other restrictions described below. To illustrate method translation, let $T_1(t)$ and $T_2(t)$, where t is time since injection of the mixture in a column, be the temperature programs in methods 1 and 2, respectively. Let also $t_{M1,ref}$ and $t_{M2,ref}$ be, respectively, reference void times in methods 1 and 2. These quantities should be isothermally measured at the same reference temperature. If the following conditions are met:

a. the capillary columns have the same type of a liquid stationary phase;

b. the ratio of a column internal diameter and the stationary phase film thickness is the same, i.e. $d_{c1}/d_{f1}=d_{c2}/d_{f2}$;

c. column inlet and outlet pressure remain constant during the analysis (this is known as a constant pressure mode); and d. temperature programs $T_1(t)$ and $T_2(t)$ relate as $T_2(t) = T_1(G \times t)$ where $G=t_{M2,ref}/t_{M1,ref}$ (for a piece-wise linear temperature program, this means that all temperature plateaus in method 2 are G-fold shorter than their counterparts in method 1, and all temperature ramps in method 2 have G-fold higher heating rates than their counterparts in method 1), then retention time, $t_{R2}$, of any peak in method 2 can be found as $t_{R2}=t_{R1}/G$ where $t_{R1}$ is retention time of the peak corresponding to the same solute in method 1. Two methods satisfying this set of conditions are known as mutually translatable methods, and each of the two methods is known as a translation of the other, where quantity $G=t_{M2,ref}/t_{M1,ref}$ is known as a speed gain in method 2 relative to method 1.

While the above-mentioned restrictions disallow some differences in parameters for the methods to be mutually translatable, the restrictions do not prevent many other important differences. Thus, mutually translatable methods may use columns with different diameters and lengths, may use different types of carrier gas (helium, hydrogen, nitrogen, etc.), may have different flow rates as well as different inlet pressures and outlet pressures. The latter includes the cases when, in one of the mutually translatable methods, outlet is at the vacuum while in another the outlet is at an ambient or at any other constant pressure. A theoretical analysis of the method translation is described in Blumberg, L. M. and Klee, M. S., "Method Translation and Retention Time Locking in Partition GC", Analytical Chemistry, vol. 70, number 18, Sept. 15 1998, pp.

3828–3839. An algorithm for the calculation of the temperature program in a translated method from that of an original method, and from the ratios of the column dimensions and other relevant parameters of the two methods, is also described in U.S. Pat. No. 5,405,432.

Method translation has several useful properties. It can be viewed, for example, as a G-fold compression (stretching, if G<1) of the time axis of a temperature program in a translated method compared to that in the original method while keeping the temperature axis unchanged. More specifically, method translation does not change initial and final temperatures preceding and following each temperature ramp. It only reduces the duration of each temperature plateau and increases the heating rate of each temperature ramp by the same factor equal to the speed gain, G.

Method translation has similar time scaling effect on peak retention times. Specifically, it reduces (increases, if G<1) all retention times in a translated method by the same speed gain G. This suggests that the calibration table for a translated method can be regenerated from the calibration table of the original method by simply dividing each retention time entry in the original calibration table by the same factor G. The fact that the translated method runs G times faster (if G>1) than the original one, is the reason to refer to G as to the speed gain.

Method translation can be viewed as proportional compression (stretching, if G<1) of the chromatographic time axis by a fixed factor equal to speed gain, G, defined as the ratio of original and translated void times measured at the same temperature. Simply stated, method translation allows an increase of the speed of analysis by a factor of G. Practical examples having G higher than 10 are known from the literature.

Another beneficial view of method translation can be described using the concept of a peak retention pattern. Rather than expressing the chromatographic time, t, in absolute time units (seconds, minutes, etc.), one can express it in the units of a reference void time, $t_{M,ref}$, using dimensionless time $x=t/t_{M,ref}$ instead of t. A temperature program where time is expressed in these dimensionless units is known as a normalized temperature program. As long as the reference void times in all mutually translatable methods are measured at the same temperature, all these methods (a) have the same normalized temperature program and (b) yield the same dimensionless retention time for the same solute.

A sequence of dimensionless retention times for a given sequence of solutes is known as a peak retention pattern for those solutes. As long as the reference void times in the mutually translatable methods are measured at the same temperature, all those methods yield the same retention pattern for the same sequence of solutes. As a result, the dimensionless retention time entries in the calibration tables of the mutually translatable methods are the same, and, hence, there is no need to regenerate those entries for each particular translation of the same method.

Sometimes, rather than expressing retention times, $t_{RA}$, $t_{RB}$, $t_{RC}$, etc. and retention patterns in dimensionless units $X_{RA}=t_{RA}/t_{M,ref}$, $X_{RB}=t_{RB}/t_{M,ref}$, $X_{RC}=t_{RC}/t_{M,ref}$, etc., respectively, it is chromatographically more meaningful and convenient to use dimensionless quantities $k_{RA}=t_{RA}/t_{M,ref}-1$, $k_{RB}=t_{RB}/t_{M,ref}-1$, $k_{RC}=t_{RC}/t_{M,ref}-1$, etc., respectively. These quantities are known as peak retention factors. An additional discussion of peak retention patterns can be found in Blumberg, L. M. and Klee, M. S., "Method Translation and Retention Time Locking in Partition GC", Analytical Chemistry, vol. 70, number 18, Sept. 15, 1998, pp. 3828–3839. Utilization of retention factor databases for the sample identification in GC is described in U.S. Pat. No 6,153,438.

Dimensionless times can be used for the expression of other time events during a GC analysis. This, in turn, allows for a generic description of GC methods where a description based on the dimensionless time is used as a description of the unique core of all mutually translatable methods. A normalized temperature program and a normalized calibration table would be the components of the core description of a method. The particulars (the column dimensions, the carrier gas type and its inlet and outlet pressure) of the different translatable implementations of the same method can be supplied as conditions in each particular analysis based on the same core method. Manipulation of the particular parameters allows speeding-up or slowing-down the analysis, trading separation for time, or either of those for the sample capacity, etc.—all without affecting the peak retention pattern and a normalized calibration table. This allows, for example, a faster analysis with lower separation for many repetitive trials during the method development, and upgrading of the final analysis to the required separation. This also allows for a transparent pressure optimization (manual and/or automatic) in a temperature programmed analysis as described below.

It is known from GC theory how to approximately find the flow rate (or, equivalently, velocity, pressure, etc.) of a carrier gas that results in the best separation of a given (typically, the most critical) pair of solutes, in a given separation of that pair in the shortest time, etc. This optimization is based on the analysis of the plate height vs. flow rate, plate duration vs. flow rate, and similar curves. An experimental evaluation of these curves allows for an additional fine-tuning of these optimization techniques. Typically, these curves are evaluated only for the isothermal conditions leading to recommendations that might not be optimal under the temperature programmed conditions. A better approach can be to, first, develop a temperature program for some fixed pressure, and then further optimize the pressure for a particular (possibly, most critical) pair of peaks using translatable variations of the pressure. These variations allow for further optimization of the separation without changing the peak retention pattern in the entire chromatogram.

Another benefit of method translation is its use for retention time locking. Several realizations of nominally the same method can yield different retention times for the same solute, and different retention patterns for the same mixture. For example, due to specifics of column manufacturing, two nominally identical columns can have different actual internal diameters and lengths. Used in two nominally identical GC systems these columns can yield different void times even in nominally identical methods. The pressure measurement errors in those GC systems can further magnify the void time difference. That difference in otherwise identical methods can result in a retention pattern difference yielded by these methods. According to the method translation, adjusting the inlet pressure in each nominally identical method to yield the same reference void time as that in another nominally identical method substantially reduces the retention time differences in all such methods. This process, known as retention time locking (RTL), can also be viewed as a reverse method translation where, instead of the rescaling the temperature program to adopt to the changes in the void time, the latter is adjusted to adopt to a fixed temperature program. A theoretical study of RTL can be found in Blumberg, L. M. and Klee, M. S., "Method Translation and Retention Time Locking in Partition GC", Analytical Chemistry, vol. 70, number 18, Sept. 15, 1998, pp. 3828–3839. Several implementations of RTL are described in U.S. Pat. Nos. 5,827,946, 5,987,959, 6,036,747, and 6,153,438.

Benefits of Conventional Method Translation

Conventional method translation allows an increase in the speed of analysis (some times by a factor of 10 or more) with no or little additional method development while preserving the solute elution pattern and resolutions of all peak pairs. Method translation also allows a trade-off of separation for time and vice versa, or either of those for the sample capacity, etc.—all without affecting the solute elution pattern and requiring little or no additional method development. (In the original method development, this can be used for fast repetitive trials until the best conditions are found and then upgrading the final conditions to achieve a required separation. In testing of large numbers of samples, it can be used for fast screening with lower resolution followed by more accurate analysis of only the selected samples.) Method translation also facilitates porting of GC methods from one set of conditions (different instruments, different columns, different ambient environment, etc.) to another. Method translation may be made to appear transparent. All mutually translatable methods can be expressed via a unique normalized temperature program (a temperature program expressed in terms of dimensionless time) which can be treated as a core of all mutually translatable methods.

A transparent pneumatic optimization (optimization of a carrier gas flow rate, velocity, pressure, etc.) of a column may be performed in isothermal or temperature programmed analysis in order to achieve the best tradeoff between the shortest possible analysis time and adequate separation of a given (typically the most critical) pair of peaks without any change in a peak elution pattern. In addition to that, Retention Time Locking (RTL) is just one of several implementations of method translation.

Shortcomings of Conventional Method Translation

Unfortunately, the currently known method translation algorithms are very restrictive. The key requirement for the currently known method translation and RTL algorithms is that the ratio, $t_{M1}/t_{M2}$, of the void times measured at the same temperature in two mutually translated methods 1 and 2, respectively, be the same for all temperatures. This leads to the requirement for constant pressure mode in order for a method to be translatable.

One of the most practically important departures from the constant pressure mode is a constant flow mode of a GC analysis where the carrier gas flow rate measured at some predetermined conditions (typically, atmospheric pressure, and 0° C. or 25° C.) remains constant during a temperature programmed analysis. Constant flow mode has many advantages over the constant pressure mode. As a carrier gas viscosity increases with temperature, the column pressure increases with temperature in order to maintain the constant flow. Most contemporary GC instruments are equipped with the electronic pressure control (EPC) regulators that allow implementation of constant flow mode. Unfortunately, currently known method translation and RTL algorithms do not preserve the peak retention pattern (the main task of the method translation) in a constant flow mode.

Occasionally, pressure programming is used to further speed-up a temperature programmed analysis. Unfortunately, currently known method translation and RTL algorithms might not work in the presence of an arbitrary pressure program.

Furthermore, the key requirement of the temperature-independence of the ratio, $t_{M1}/t_{M2}$, imposed by currently known method translation and RTL algorithms leads to the requirement that the ratio, $\eta_1/\eta_2$, of viscosities, $\eta$, of different types of the carrier gas used in two mutually translatable methods 1 and 2, respectively, be independent of temperature. This narrows the choice of the types of the carrier gas that allow the use of the currently known method translation algorithms.

Previously known method translation techniques in gas chromatography (GC) only translated between constant pressure mode methods where column pressure remains fixed during the analysis. Due to this limitation and other shortcomings of known method translation techniques, there exists a need for a method translation technique that can translate between methods, regardless of whether the methods are run in constant pressure mode.

SUMMARY OF THE PRESENT INVENTION

The present invention is directed to a new GC method translation technique that eliminates the need for a constant pressure mode, the need for a temperature-independent ratio of carrier gas viscosities, and other shortcomings of the currently known method translation techniques and RTL techniques. Elimination of these restrictions comes from the elimination of the key requirement of the currently known method translation and RTL algorithms that the ratio, $t_{M1}/t_{M2}$, of void times, $t_{M1}$ and $t_{M2}$, measured at the same temperature in two mutually translated methods 1 and 2, respectively, be temperature-independent.

Two mutually translatable GC methods 1 and 2, subject to the new method translation technique, may have void times $t_{M1}$ and $t_{M2}$, respectively, that change independently during the analysis.

The basis for method translation is preservation of the elution temperatures, $T_e$, of all solutes of interest. The latter is the column temperature at retention time, $t_R$, of the peak corresponding to the solute. Two methods are mutually translatable if, in both methods, any solute elutes at the same temperature. While the emphasis of the previously known method translation and RTL algorithms was prediction and preservation of retention times, the new technique focuses directly on preservation of the solute elution temperatures. This, in turn, leads to a more universal method translation techniques that allows an arbitrary pressure program during a temperature program.

An elution pattern for a given sequence of solutes is a sequence of respective elution temperatures of these solutes. All mutually translatable methods yield the same solute elution pattern for the same mixture. With the focus in the new method translation on the elution temperature (rather than the retention times as in the previously known techniques), the previously known RTL (retention time locking) is being replaced by elution pattern locking (EPL). The latter is more universal and easier to maintain than the former.

When two mutually translatable temperature programmed GC analyses are allowed to have mutually independent pressure programs, the only leverage for maintaining the same elution temperature for each solute in both analyses is adjusting the heating rate in the translated analysis. As a result, a translation of a linear temperature ramp (i.e. the one that has a fixed heating rate) might be a temperature vs. time curve where the heating rate gradually changes with time. Most commercially available GC system are designed to provide only a limited number (typically 3 to 6) of linear temperature ramps preceded and/or followed by temperature plateaus. In order to take a full advantage of the new method translation and EPL, a GC system should be capable of a transparent gradual variation of a column temperature (i.e., a temperature vs. time curve). This can be implemented in the same manner as the column pressure is changed during the analysis to maintain a constant flow rate.

According to one aspect of the present invention, translation may be performed to and from the methods with arbitrarily different pressure and flow programs. This includes the translation of pressure programmed methods into the flow programmed methods and vice versa, translation of a constant pressure mode into a constant flow mode (carrier gas flow remains fixed during the analysis) and vice versa, translation from the constant flow mode with one flow rate to the constant flow mode with another flow rate, etc.

According to another aspect of the present invention, translation to and from the methods may be performed with a wider choice of carrier gas types.

According to a further aspect of the present invention, all methods can be implemented as different specific executions of the same normalized temperature program. No explicit translation of one method into another is necessary. Elution pattern locking is automatic.

According to yet another aspect of the present invention, a method can be designed to generate a solute elution pattern that is unique for all mutually translatable methods. This allows elimination of the need for a change of a calibration table when method parameters (column dimensions, carrier gas type, pressure program, etc.) are changed.

According to a further aspect of the present invention, GC system resources may be better utilized. If, for example, an oven heating rate required by a temperature program exceeds a maximum available in a given instrument, a heating (linear or ballistic) rate that is lower than the required rate can be allowed. In order to preserve the elution pattern, the pressure program can automatically compensate for the departure of the temperature program from its nominal settings. This allows the use of temperature programs that exploit the actually available maximum heating rate instead of the guaranteed maximum heating rate which is, typically, substantially lower than the actually available one.

According to yet another aspect of the present invention, a transparent pneumatic optimization (optimization of a carrier gas flow rate, velocity, pressure, etc.) of a column in isothermal or temperature programmed analysis may be performed in order to achieve the best tradeoff between the shortest possible analysis time and adequate separation of several (typically the most critical) pairs of peaks.

According to a further aspect of the present invention, Elution Pattern Locking (EPL) for an arbitrary pressure/flow regulation includes constant pressure and constant flow modes.

DETAILED DESCRIPTION OF ILLUSTRATIVE EMBODIMENTS

To describe the embodiments of the present invention, the following symbols will be used, as shown below in Table 1.

TABLE 1

| Symbol | Description | units |
|---|---|---|
| d | Characteristic cross-sectional dimension of a column, Eqs. (6) and (7) | length |
| $d_c$ | Column internal diameter | length |
| $d_f$ | Stationary phase film thickness | length |

TABLE 1-continued

| Symbol | Description | units |
|---|---|---|
| $d_p$ | Particle size of a column packing material | length |
| F | Flow rate (typically, volumetric) of carrier gas | volume/time |
| J | Flux (typically, volumetric) of carrier gas, Eq. (12) | length/time |
| k | Retention factor | none |
| L | Column length | length |
| $N_b$ | Basic plate number of a column, Eq. (5) | none |
| $p_a$ | Ambient pressure | pressure |
| $p_c$ | Compressed pressure drop, Eq. (2) | pressure |
| $p_h$ | Column head pressure | pressure |
| $p_i$ | Column inlet pressure | pressure |
| $p_o$ | Column outlet pressure | pressure |
| $p_{ref}$ | Reference pressure | pressure |
| $\Delta p_d$ | Detector pressure drop | pressure |
| R | Heating rate | Temperature/time |
| r | Normalized heating rate, Eq. (24) | temperature |
| T | Column temperature | temperature |
| $T_e$ | Elution temperature of a solute | temperature |
| $T_{ref}$ | Reference temperature | temperature |
| t | Time | time |
| $t_M$ | Void time | time |
| $t_{max}$ | Time of analysis | time |
| $t_p$ | Duration of a temperature plateau | time |
| $t_R$ | Retention time | time |
| $\epsilon$ | Porosity of column packing, Eqs. (15) and (16) | none |
| $\mu$ | Solute mobility factor | none |
| $\eta$ | Gas viscosity | pressure · time |
| $\tau$ | Dimensionless time Eq. (22) | none |
| $\phi$ | Resistance factor of a column, Eqs. (6) and (7) | none |
| $\Omega$ | Volumetric resistance of a column, Eq. (14) | pressure · time/length |
| $\omega$ | Quantity defined in Eq. (4) | pressure · time |

Void Time

In a temperature and pressure programmed analysis, void time (the time of migration of an unretained solute from the inlet to the outlet of a column) at any given time, t, is measured at a pressure and a temperature existing at time t. This means that whether $t_M$ is a fixed void time in a constant pressure isothermal analysis, or it is a quantity that changes with time in a pressure and temperature programmed analysis, each particular value of $t_M$ always represents the void time under a particular pressure and temperature.

Calculation of Void Time in a Pressure Programmed System

Void time, $t_M$, can be calculated as:

$$t_M = \omega/p_c \quad (1)$$

where $p_c$ is a compressed pressure drop that can be calculated as:

$$p_c = \frac{3}{4} \cdot \frac{(p_i + p_o)^2}{p_i^2 + p_i p_o + p_o^2} \cdot (p_i - p_o) \quad (2)$$

where $p_i$ and $P_o$ are, respectively, the column's inlet and outlet pressure. In many cases, column head pressure, $p_h$, defined as $p_h = p_i - p_a$ where $p_a$ is ambient pressure, is used as an independent control parameter. In that case $p_i$ can be calculated as:

$$p_i = p_a + p_h \quad (3)$$

Eq. (2) allows finding $p_c$ from a known $p_o$ and $p_i$. A conversion of $p_c$ and $p_o$ into $p_i$ is described in the literature (See, e.g., Eq. (55) with $\bar{ru} = p_c$ in Blumberg, L. M., "Relations between Pneumatic Parameters of Ideal Gas in a Column with Uniform Permeability", *Chromatographia* 41, No 1/2, July 1995, pp. 15–22). An alternative (and better in some respects) approach would be to treat $p_c$ within a GC system as an independent pneumatic control parameter. Quantity ω in Eq. (1) can be calculated as:

$$\omega = \phi N_b^2 \eta \quad (4)$$

In this formula, η is viscosity of the carrier gas, φ is a dimensionless constant that can be interpreted as a resistance factor of the column, and $$N_b = L/d \quad (5)$$

where $N_b$ is the basic plate number, L is column length, and d and is the characteristic cross-sectional dimension of the column. For capillary columns:

$$\phi = 32, d = d_c \text{ (capillary columns)} \quad (6)$$

where $d_c$ is column diameter. For packed columns, φ depends on the type of a packing and can be different for two columns even if they are packed with material of the same type and with the same particle size, $d_p$. As a result, only an approximate value of φ can be a priori known. For packed columns:

$$\phi \approx 3000, d = 2d_p \text{ (packed columns)} \quad (7)$$

Frequently (especially in the case of packed columns), some or all parameters, φ, $N_b$, and η, required for the calculation of ω in Eq. (4) are not known with the desired accuracy. In that case, ω can be experimentally found by measuring $t_M$ at a known compressed pressure drop $p_c$, and using the formula:

$$\omega = p_c t_M \quad (8)$$

Typically, φ and $N_b$ in Eq. (4) do not depend on temperature, T, while viscosity, η, does in a significant way. If η for the carrier gas utilized in the method is known, the product $\phi N_b^2$ can be calculated as:

$$\phi N_b^2 = \eta/\theta = p_c t_M/\eta \quad (9)$$

Otherwise, one needs to find the dependence of η on T by making several measurements of ω for different temperatures and calculating η using the expression:

$$\eta = \omega/(\phi N_b^2) = p_c t_M/(\phi N_b^2) \quad (10)$$

Flow Programmed Systems

Instead of pressure, a flow rate of a carrier gas is frequently used in GC as an independent pneumatic control parameter. Although void time, $t_M$, can be calculated directly from the flow rate, calculation of $p_c$ from the flow rate and then using the above described procedures for the calculation of $t_M$ from $p_c$ leads to more uniform algorithms.

To achieve a certain value of the flow rate for a given set of conditions, a certain pressure is required. If the conditions change with time, then the pressure becomes a time-dependent quantity even if the flow remains constant. This pressure, internally measured within a GC instrument, can be treated as an independent quantity even in a flow programmed analysis.

If necessary, the pressure can also be calculated from a known combination of flow and temperature programs. The calculation of the pressure depends on a particular type of the flow rate. Some flow rate types are described in Blumberg, L. M., "Flow Rate and Velocity of ideal Gas in a Capillary Column with Uniform Permeability, J. High Resolut. Chromatogr. 22, No. 4, 1999, p. 213–216". The type most frequently used in GC is a volumetric flow rate, F, measured at a predetermined reference pressure, $p_{ref}$, and reference temperature, $T_{ref}$. (Typically, $P_{ref}=1$ atm while $T_{ref}=0°$ C. or $T_{ref}=25°$ C.).

To enable the treatment of the flow rate in capillary and in packed columns in a similar way, it is convenient to deal with the flux, J,—the flow per unit of cross-sectional area of a column—rather that with the flow rate, F, itself. The latter two relate as:

$$F = (\pi/4) d_c^2 J \quad (11)$$

or, inversely, as:

$$J = 4F/(\pi d_c^2) \quad (12)$$

where $d_c$ is internal diameter of a (packed or capillary) column. The flux can be calculated as:

$$J = \frac{T_{ref}}{T} \cdot \frac{1}{\Omega} \cdot \frac{p_i^2 - p_o^2}{2 p_{ref}} \quad (13)$$

where $$\Omega = \frac{\phi L \eta}{\varepsilon d^2} \quad (14)$$

and Ω can be viewed as a flow resistance of the column that has characteristic cross-sectional dimension d (Eqs. (6) and (7)), and porosity ε. For capillary columns, $$\varepsilon = 1 \text{ (capillary columns)} \quad (15)$$

and for packed columns, ε depends on many factors. As a first approximation, it can assumed that $$\varepsilon \approx 0.4 \text{ (packed columns)} \quad (16)$$

In addition to (or instead of) direct calculation of flow resistance, Ω, from Eq. (14), it can also be found from quantity ω in Eq. (4) as:

$$\Omega = \omega/(\varepsilon L) \quad (17)$$

If the product εL is not known for a given column (for a capillary columns, ε=1) then it can be found experimentally by measuring J at an arbitrary pressure and temperature and calculating Ω from the expression:

$$\Omega = \frac{T_{ref}}{T} \cdot \frac{p_i^2 - p_o^2}{2 p_{ref}} \cdot \frac{1}{J} \quad (18)$$

and then calculating εL from:

$$\varepsilon L = \omega/\Omega \quad (19)$$

where ω corresponds to the same experimental conditions. Both Ω and ω are proportional to gas viscosity. If the temperature dependence of viscosity is not known, one of the quantities Ω or ω should be measured for several temperatures. The other can be found from the measurement at a single temperature and the expression:

$$\omega = (\varepsilon L) \Omega \quad (20)$$

or from Eq. (17). After performing these measurements and calculations, Ω (as well as ω, as described earlier) can be treated as a known quantity. With that, the column pressure can be calculated for each value of carrier gas flux, J, and column temperature, T, as:

$$p_i = \sqrt{p_o^2 + 2p_{ref}\Omega JT/T_{ref}} \quad (21)$$

This together with Eqs. (1) and (2) allows calculation of void time from pressure when the flow rate is an independent control parameter.

Actual and Dimensionless Time

As described above, void time, $t_M$, is a convenient time unit that can be used as a basis for defining a dimensionless time in chromatography. Many concepts, including the concept of method translation, are easier to describe in terms of dimensionless time. Small increments, dt and dτ, in actual time, t, and in dimensionless time, τ, relate as $d\tau = dt/t_M$. When void time is known, t can be transformed into τ as:

$$\tau = \int_0^t dt/t_M \quad (22)$$

On the other hand, τ can be transformed into t as:

$$t = \int_0^\tau t_M d\tau \quad (23)$$

Components of a Temperature Program in GC

Two types of segments can be identified in any temperature program expressing a column temperature, T, as a function of time, t. There are the temperature ramps—the segments where a column temperature changes with time, and the temperature plateaus—the segments where the temperature remains constant.

Using the transformations in Eqs. (22) and (23), a duration, $t_p$, of each temperature plateau expressed in units of actual time can be transformed into a dimensionless duration, $\tau_p$, and, vice versa, $\tau_p$ can be transformed into $t_p$.

Typically, the heating rate, R, defined as R=dT/dt, remains fixed during a given temperature ramp. However, it does not have to be so, and the full benefit of the method translation of the present invention can be realized only when a gradual time-dependent variation of R is allowed. Although a method translation can be easily adopted to handle non-monotonic (rising and falling heating ramps), there is no apparent need in current GC to consider falling temperatures. To illustrate the method translation techniques of the present invention, rising temperature ramps are considered below.

A transformation of:

$$r = t_M R \quad (24)$$

allows transformation of an actual heating rate, R, (measured in units of temperature/time) into a normalized heating rate, r, (measured in units of temperature per void time). An inverse transformation is described by the formula:

$$R = r/t_M \quad (25)$$

Typically, a temperature program in GC is described as a combination of functions of time and temperature: the plateaus are typically described as functions of time (example: 1 min at 100° C.) while the temperature ramps are described as functions of temperature (example: ramp at 10° C./min until reaching 200° C.). In addition, a temperature program can be described strictly as a function, T(t), of time (example: 1 min at 100° C., 10 min at 10° C./min). It can be also convenient, especially for computer execution, to express the same function, T(t), as a sequence of (t, T)—pairs such as ((0 min, 100° C.), (1 min, 100° C.), (11 min, 200° C.)). Along with this sequence, certain interpolation rules between the tabulated points (such as a linear or a spline interpolation) can be specified as a part of a GC method. The sequence of (t, T)—pairs along with the predetermined interpolation rules can be viewed as an expression of a column temperature, T, as a function, T(t), of time, t, or, vice versa, as an expression of time as a function, t(T), of column temperature, T. These treatments of temperature are generally the most transparent and allow the most straightforward computer implementation. Although method translation does not require any particular implementation of a temperature program, the implementation of it as an a priori known mathematical function T(t) or a (t, T)-table (a collection (t, T)-pairs) is treated as a starting point in this embodiment of the method translation technique.

Using the transformation described in Eq. (22), a T(t) function as well as a (t, T)-table can be transformed into a T(τ) function or (τ, T)-table where τ is dimensionless time. A temperature program expressed in terms of τ and T, is a normalized temperature program. Similarly to the expression t(T), a normalized temperature program can be interpreted as a function, τ(T), describing the dependence of τ on T.

Elution Patterns

An elution pattern for a sequence of solutes eluting during a GC analysis is a sequence of respective dimensionless elution times. (From the basic concept of method translation, it can make more sense to deal with an alternative thermal elution pattern—a sequence of elution temperatures of the respective solutes in a given analysis. Unfortunately, an ambiguity might arise in a thermal elution pattern during a temperature plateau where more than one solute might elute at the same temperature. The ambiguity can be resolved by combining thermal elution patterns for all heating ramps with temporal elution patterns for all temperature plateaus. In this case, the time in each temporal elution pattern can be counted from the beginning of each plateau.)

Method Translation

Two GC methods or two GC analyses that result in the same elution pattern for any given solute mixture are mutually translatable ones or, equivalently, are translations of each other.

A mutual translatability of two GC method can be described in terms of the solute mobility factors. Typically, retention of a solute in a column at a given temperature is described by a retention factor, k. A solute mobility factor, $\mu$, relates to k as $\mu = 1/(1+k)$. Additional discussion of the properties of $\mu$ can be found in Blumberg, L. M. and Klee, M. S., "Elution Parameters in a Constant Pressure, Single-Ramp Temperature-Programmed Gas Chromatography", Journal of Chromatography A, vol. 918/1 (2001), p. 113–120.

Method translation can be viewed as a derivation of method parameters for one GC method from those of another method. A derived GC method with a normalized heating rate, r, is a translation of an original GC method with a normalized heating rate, $r_0$, if both methods have such temperature programs that, for each solute having mobility factors $\mu_o$ and $\mu$, in, respectively, the original and the derived methods satisfy the following two conditions:

C1. for the same column temperature during any temperature ramp:

$$\mu/r = \mu_o/r_o \quad (26)$$

and

C2. dimensionless durations, $\tau_{p,o}$ and $\tau_p$, of any two temperature plateaus taking place at the same temperature in the original and the derived methods, respectively, are governed by:

$$\mu\tau_p = \mu_o\tau_{p,o} \quad (27)$$

Typically, mobility factors of unknown solutes are beyond the control of a method developer, and, hence, the above specified conditions C1 and C2 can not be predictably satisfied for an arbitrary pair of columns. Two columns are considered to be mutually translatable or, equivalently, translations of each other if at any temperature, T, any solute has the same mobility factor, $\mu$, in both columns. For capillary and packed columns with liquid stationary phase, this requirement is satisfied if both columns have the same stationary phase type, and the same phase ratio (a ratio of the volumes of mobile and stationary phases). For columns with porous solid stationary phases, different types and levels of the stationary phase porosity should be taken into account.

Importantly, the necessary conditions for the translatability of the methods utilizing mutually translatable columns become very simple. That is, all methods utilizing mutually translatable columns are mutually translatable if they have the same normalized temperature program (i.e. the one expressed in terms of $\tau$ and T).

Unlike the restrictive conditions of currently known method translations (constant pressure only), the method translation of the present invention has no restrictions on pressure (or flow) variations in two mutually translatable methods. The method translation of the present invention also substantially relaxes the requirements on temperature programs in mutually translatable methods. The only requirement for temperature programs in two mutually translatable methods is that they should cover the same temperature range, and should have plateaus at the same temperature. The durations of the temperature plateaus as well as temperature profiles during the temperature ramps in two mutually translatable methods can be arbitrarily different.

To confirm that, for two mutually translatable methods having arbitrarily different temperature programs, the conditions of method translation are satisfied (and, hence, both methods yield the same solute elution pattern), both methods should have pressure/flow programs that are translations of each other. In an alternative approach, an arbitrary pressure (or flow) program can be chosen for a translated method while using an appropriate translation of the temperature program to satisfy the method translation conditions. These options, together with the choice of arbitrarily different column dimensions and types (capillary or packed), as well as the carrier gas types, opens a great flexibility in the selection of parameters for a translated method.

System resources (limited maximum pressure, limited heating rate, etc.) can impose some restrictions on the choice of the original and translated method parameters. Requirements for a column optimization can impose additional restrictions on the selection of the column parameters (e.g., flow rate should be in a certain relation to a column diameter, normalized heating rate should not be very far from 10° C. per void time, etc.). However, these restriction are external for the method translation (i.e. are not necessary for the preservation of the elution patterns).

Elution Pattern Locking (EPL)

Typically, only the nominal values of column dimensions and other column parameters are known from column manufacturers. However, in many cases, the supplied data is not sufficiently accurate for accurate reproduction of the solute elution pattern resulting from nominally the same analyses using different instruments. This is especially true for packed columns where only rough estimates of the particle size, $d_p$, and resistance factor, $\phi$, are known for each particular column. In addition, column parameters may vary over time. For example, a capillary column can be trimmed from time to time. This can cause a gradual departure from the nominal elution pattern. An accurate verification of the product $\phi N_b^2$ followed by the method translation to accommodate the differences can substantially improve the reproducibility of the elution pattern for the same solute mixture. This process can be viewed as elution pattern locking (EPL) and may be considered analogous to RTL described above. The verification of $\phi N_b^2$ for the EPL (either after the installation of a new column, or on a periodic basis) can be done via the measurement of $t_M$ at an a priori known $p_c$ and calculating $\phi N_b^2$ from Eq. (9), or by other means such as measurement of actual retention times of known peaks under the predetermined conditions.

Method Translation via a Normalized Temperature Program

The specifics of each particular method (e.g., particular column dimensions, carrier gas type, pressure program, etc.) can be reduced to its void time, $t_M$, expressed as a function of actual time, t, or dimensionless time, $\tau$. A combined representation of $t_M$ (for example, as a function of T during the temperature ramps, and of $\tau$ during the plateaus) is also possible.

In practice, however, GC methods are typically described not in terms of $t_M$, but rather in terms of actual column dimensions, actual carrier gas type, etc. These options are typically combined with the choice of pressure or temperature as a control parameter with both allowed to be programmed in time or as functions of each other.

The number of independent variables (time, temperature or their combination), control parameters (pressure or flow), column dimensions and types (capillary or packed), carrier gas types, etc., combined with nearly unlimited choice of temperature or pressure/flow programs in a translated method opens an abundance of specific method translation algorithms and EPL strategies. Moreover, to save the computing load during the real time execution of the analysis, the algorithms can be implemented either in a GC processor or another processor, or some combination thereof.

To better structure the descriptions of method translation and EPL algorithms, all method translation procedures can be broken into two steps (although a direct translation from one set of specific data to another is also possible, as shown in an example below).

In the first step, an actual temperature program, $T_o(t)$, in a method that serves as an origin for all other mutually translatable methods is translated into a normalized temperature program, $T(\tau)$. The translation takes into account all specific conditions (column dimensions, carrier gas type, pressure or flow program, etc.) of the original method.

In the second step, all unknown parameters of a translated method are calculated based on its known specific parameters, and on the normalized temperature program, $T(\tau)$, that is the same for all mutually translatable methods. The known specific parameters of a given translated method can be its column dimensions, carrier gas type, pressure or flow programs, etc. In this case, the method translation results in the calculation of a translated temperature program, T(t), that is specific for this particular translation. In another case the temperature program, T(t), of the translated method can be arbitrarily (within the above described restrictions to the choice of the temperature plateaus and the overall temperature range) chosen by the method developer. In this case, the method translation results in the calculation of a translated pressure or flow program as requested by the operator.

This two step approach makes logical sense, and has many practical advantages as well. For a method described in terms of a normalized temperature program, a practical implementation of its translation into any other method and its EPL become only a matter of difference in the specifics of execution of the same normalized temperature program.

To further reduce the number of different algorithms, no special treatment for isothermal analyses as well as for the ones with constant pressure or flow is provided (although the simplifying shortcuts are, obviously, possible). For example, a $(t, T)$-table, $T(t)$, describing a temperature program in a $t_{end}$-long isothermal analysis at temperature $T$ might look like $T(t) = ((0, T), (t_{end}, T))$. A corresponding $(\tau, T)$-table describing a normalized temperature program in the same analysis might look like $T(\tau) = ((0, T), (\tau_{end}, T))$. A change in a pressure program in this analysis might change the value of tend, but it will not affect the value of $r_{end}$.

Embodiments of Translation of Actual Temperature Program, T(t), into a Normalized Temperature Program, $T(\tau)$ In one embodiment of the present invention (Case A), a Normalized Temperature Program, $T(\tau)$, is generated based on a given pressure and temperature program in a first method as set forth below.

---

Case A

Known Parameters:
Inlet pressure, $p_i(t)$, and outlet pressure, $p_o(t)$, (typically, $p_o$ is fixed during a given analysis)
Column parameters:
   length, L
   characteristic dimension, $d = d_c$ (capillary columns),
   or $d = 2d_p$ (packed columns)
   resistance factor, $\phi$ (for capillary columns, $\phi = 1$)
Temperature Program, T(t)
Carrier gas type and its viscosity, $\eta(T)$, as a function of temperature
All functions can be expressed in a mathematical or tabular form. In the latter case, a table can be accompanied by the rules of interpolation (say, a cubic spline) between the tabulated points
MATHEMATICAL SOLUTION:
$\omega(t) = (L/d)^2 \phi \eta(T(t))$ $$^*p_c(t) = \frac{3}{4} \cdot \frac{(p_i(t) + p_o(t))^2}{p_i^2(t) + p_i(t)p_o(t) + p_o^2(t)} \cdot (p_i(t) - p_o(t))$$

$t_M(t) = \omega(t)/p_c(t)$ $$\tau(t) = \int_0^t dt/t_M(t)$$

$t(\tau)$ is an inversion of $\tau(t)$
$T(\tau) = T(t(\tau))$
*NOTE: Skip this step if $p_c(t)$ (rather than $p_i(t)$ and $p_o(t)$) is a known pressure program
NUMERIC SOLUTION
Initialization: $a = (L/d)^2 \phi$, $t = 0$, $\tau = 0$, extract $t_{max}$ from T(t), initialize empty $(\tau, T)$-table
Loop:
T = T(t)
Insert $(\tau, T)$ into $(\tau, T)$-table
If $t = t_{max}$ then Exit the Loop -continued Case A $^*p_o = p_o(t)$
$^*p_i = p_i(t)$ $$^*p_c = \frac{3}{4} \cdot \frac{(p_i + p_o)^2}{p_i^2 + p_i p_o + p_o^2} \cdot (p_i - p_o)$$

$\eta = \eta(T)$, $\omega = a\eta$
$t_M = \omega/p_c$
If $t + \Delta t \geq t_{max}$ then $\Delta t = t_{max} - t$ (last step)
$t = t + \Delta t$
$\tau = \tau + \Delta t/t_M$
End of the Loop
NOTES:
The steps marked with asterisk (*) should be replaced with the step $p_c = p_c(t)$ if $p_c(t)$ (rather than $p_i(t)$ and $p_o(t)$) is a known pressure program.
The size of the time increment, $\Delta t$, and/or some details of execution may be optimized for best accuracy.
There is no need to store all the data pairs generated in the $(\tau, T)$-table. Most of them can be reconstructed using the predefined interpolation rules.

---

In another embodiment of the present invention (Case B), a Normalized Temperature Program, $T(\tau)$, is generated based on a given flow and temperature program in a first method as set forth below.

---

Case B

Known Parameters:
Column internal diameter, $d_c$
Reference pressure, $p_{ref}$, and temperature, $T_{ref}$, for flow measurement
Flux J(t) of carrier gas (if flow rate, F(t), of carrier gas is known then use conversion
$J(t) = 4F(t)/(\pi d_c^2)$)
Packing porosity, $\epsilon$, (for capillary columns, $\epsilon = 1$)
All other parameters, except $p_i$, as shown in Case A.
MATHEMATICAL SOLUTION:
$\Omega(t) = L\phi\eta T(t))/(\epsilon d^2)$ $$p_i(t) = \sqrt{p_o^2(t) + 2(p_{ref}/T_{ref})T(t)\Omega(t)J(t)}$$

Continue with the Mathematical Solution as shown above in Case A.
NUMERIC SOLUTION
Everything is the same as in Numeric Solution shown above in Case A except that the step $p_i = p_i(t)$ should be replaced with the following steps:
$J = J(t)$
$\Omega = \omega/(\epsilon L)$ $$p_i = \sqrt{p_o^2 + 2p_{ref}\Omega JT/T_{ref}}$$

---

Embodiments of Execution of a Normalized Temperature Program, $T(\tau)$, With Different Specific Method Conditions The following several embodiments of translation of a known normalized temperature program, $T(\tau)$, and some specific conditions of a translated method illustrate the reconstruction of unknown method parameters (temperature or pressure/flow program). This reconstruction can also be conducted concurrently with the actual execution of the translated method. All following execution techniques are described as being driven by the increments, $\Delta t$, of actual time, t. Driving by the increments, $\Delta \tau$, of dimensionless time, $\tau$, is also possible. A $(t, \tau)$—table and a $(t, T)$—table, generated during each execution, can be used for the generation of the peak elution patterns during the processing of the chromatogram resulted from the analysis.

In another embodiment of the present invention (Case C), a Normalized Temperature Program, $T(\tau)$ is known and a temperature program T(t) for a second method, is generated based on a given pressure and temperature program in a first method as set forth below.

---

Case C: Arbitrary Pressure Program

Known Parameters:
Normalized temperature program, T(τ)
All parameters of Case A except for the temperature program, T(t), which should be regenerated during the execution
EXECUTION
Initialization: a = (L/d)²φ, t = 0, τ = 0, extract $\tau_{max}$ from T(τ),
initialize empty (t, τ)-table, and (t, T)-table
Loop:
T = T(τ) (this is the T for the current values τ and 1)
Insert (t, τ) into (t, τ)-table, and (t, T) into (t, T)-table
*$p_o = p_o(t)$
*$p_i = p_i(t)$

*$p_c = \dfrac{3}{4} \cdot \dfrac{(p_i + p_o)^2}{p_i^2 + p_i p_o + p_o^2} \cdot (p_i - p_o)$ η = η(T), ω = aη
$t_M = \omega/p_c$
If τ = $\tau_{max}$ then Exit the Loop
If τ + Δt/$t_M$ ≧ $\tau_{max}$ then Δt = $\tau_{max} t_M$ − t (last step)
t = t + Δt
τ = τ + Δt/$t_M$
End of the Loop
NOTES:
The steps marked with asterisk (*) should be replaced with the step $p_c = p_c(t)$ if $p_c(t)$ (rather than $p_i(t)$ and $p_o(t)$) is a known pressure program.
The size of the time increment, Δt, and/or some details of execution may be optimized for the best results.
There is no need to store all the data pairs generated in (t, τ)-table and/or in (t, T)-table. Most of them can be reconstructed using predetermined interpolation rules.

---

In another embodiment of the present invention (Case D), a Normalized Temperature Program, T(τ) is known and a temperature program T(t) for a second method, is generated based on a selected flow program in the second method as set forth below.

---

Case D: Arbitrary Flow Program

Known Parameters:
Normalized temperature program, T(τ)
All parameters of the Case B except for the temperature program, T(t), which should be regenerated during the execution
EXECUTION
This Execution is the same as the Execution of the Case C except, step $p_i = p_i(t)$ should be replaced with the following steps:
J = J(t)
Ω = ω/(εL)

$p_i = \sqrt{p_o^2 + 2 p_{ref} \Omega J T / T_{ref}}$

---

In another embodiment of the present invention (Case E), a Normalized Temperature Program, T(τ) is known and a pressure program for a second method, is generated based on a selected temperature program T(t) in the second method as set forth below. The selected temperature program must cover the same temperature range as the normalized temperature program and must have the same plateaus as the normalized temperature program, as described above.

---

Case E: Arbitrary Heating Rates and Plateau Durations
Known Parameters:
Normalized temperature program, T(τ)
All parameters of the Case A except for the pressure program that should be regenerated during the execution.
NOTE: According to the conditions of method translation, a specific temperature program T(t), must cover the same temperature range as the normalized temperature program, T(τ), does. Also T(t) must have the temperature plateaus at all those and only those temperatures that are the plateau temperatures in T(τ).
EXECUTION
Initialization: a = (L/d)²φ, t = 0, τ = 0, T = T(t), extract $t_{max}$ from T(t),
$t_{max,s}$ = 0, initialize empty
(t,τ)-table, and (t,T)-table
Insert (t,τ) into (t,τ)-table, and (t,T) into (t,T)-table
MAIN LOOP
If $t_{max,s}$ < $t_{max}$ then extract $t_{max,s}$ for this segment (plateau or ramp) from T(t), else Exit Main Loop
If T(t = Δt) > T then call R-Loop, else call P-Loop
End of MAIN LOOP
NOTES:
The size of the time increment, Δt, and/or some details of execution can be optimized for better accuracy of results.
There is no need to store all the data pairs generated in (t,τ)-table and/or in
(t,T)-table. Most of them can be reconstructed using the predetermined interpolation rules.
R-LOOP (Loop while in a Temperature Ramp):
If t = $t_{max,s}$ then Exit P-Loop
If t + Δt ≧ $t_{max,s}$ then Δt = $t_{max,s}$ − t (last step)
t = t + Δt
T = T(t)
Δτ = τ(T) − τ
τ = τ + Δτ
Insert (t,τ) into (t,τ)-table, and (t,T) into (t,T)-table
$t_M$ = Δt/Δτ
η = η(T), ω = aη
$p_c = \omega/t_M$ (this is the $p_c$ for the current value, t, of time)
End of R-LOOP
NOTE: $p_c$ can be converted into $p_i$, if necessary, as described in the literature (See, e.g., Eq. (55) with ru = $p_c$ in Blumberg, L. M., "Relations between Pneumatic Parameters of Ideal Gas in a Column with Uniform Permeability", Chromatographia 41, No 1/2, July 1995, pp. 15–22
P-LOOP (Loop while in a Temperature Plateau):
COMMENTS:
No restrictions on a pressure/flow program in an isothermal analysis are imposed by method translation.
No restrictions on a pressure/flow program during a temperature plateau in a temperature programmed analysis are imposed by method translation. A good choice a pressure program during a temperature plateau is a parabolic compressed pressure drop, $p_c(t)$, that provides a continuous transition from $p_{c,s}$ at the beginning of the plateau to $p_{c,e}$ at its end.
Let a given temperature plateau be the one that, in actual time, t, and in dimensionless time, τ, starts and ends at, respectively,
$t_s$, $t_e$, $\tau_s$ and $\tau_e$.
If $p_{c,s}$ and $p_{c,e}$ are compressed pressure drops at the end of the preceding temperature plateau and at the beginning of the following temperature plateau, respectively, the following program,
$p_c(t)$, provides a continuous transition from $p_{c,s}$ to $p_c$ while complying with
all the time constraints $t_s$, $t_e$, $\tau_s$ and $\tau_e$.
$p_c(t) = p_{c,s} + 2(3p_c - 2p_{c,s} - p_{c,e})\delta + 3(p_{c,s} + p_{c,e} - 2p_{c,n})\delta^2$
where $p_{c,n} = (\tau_s - \tau_e)\omega/(t_s - t_e)$
is a nominal compressed pressure drop for the plateau, and
δ = (t − $t_e$)/($t_s$ − $t_e$) is a relative time within the plateau
(this quantity changes from 0 at the beginning of the plateau to 1 at its end).
End of COMMENT
If t = $t_{max,s}$ then Exit P-Loop
If t + Δt ≧ $t_{max,s}$ then Δt = $t_{max,s}$ − t (last step)
t = t + Δt
$p_c$ = (t)
$t_M = \omega/p_c$
τ = τ + Δt/$t_M$
Insert (t,τ) into (t,τ)-table
End of R-LOOP -continued

NOTES:

$p_c$ can be converted into $p_i$, if necessary, as described in the literature (See, e.g., Eq. (55) with $\bar{n} = p_c$ in Blumberg, L. M., "Relations between Pneumatic Parameters of Ideal Gas in a Column with Uniform Permeability", Chromatographia 41, No 1/2, July 1995, pp. 15–22)

Direct Translation of a Constant Pressure Method Into a Constant Flow Method

Known Parameters of an Original Constant Pressure Method:
  Inlet pressure, $p_{i,o}$, and outlet pressure, $p_{o,o}$, - both are
  fixed during the analysis
  Column parameters:
    length, $L_o$
    characteristic dimension, $d_o = d_{c,o}$ (capillary columns),
    or $d_o = 2d_{p,o}$ (packed columns)
    resistance factor, $\phi_o$ (for capillary columns, $\phi = 1$)
  Carrier gas type and its viscosity, $\eta_o(T)$, as a function of temperature
  Temperature Program, $T_o(t)$
Known Parameters of a Translated Constant Flow Method:
  Flux, J, of a carrier gas and outlet pressure, $p_o$, - both are
  fixed during the analysis
  Column parameters:
    length, L
    characteristic dimension, $d = d_c$ (capillary columns), or
    $d = 2d_p$ (packed columns)
    resistance factor, $\phi$ (for capillary columns, $\phi = 1$)
    porosity, $\epsilon$ (for capillary columns, $\epsilon = 1$)
  Carrier gas type and its viscosity, $\eta(T)$, as a function of temperature
To be Found:
  Temperature program, T(t), of a translated method
Note: All functions can be expressed in a mathematical or tabular form.
In the latter case, a table can be accompanied by the rules of interpolation
(say, a cubic spline) between the tabulated points
GENERAL MATHEMATICAL SOLUTION FOR A HEATING RAMP
STARTING AT $T_{init}$:
For the original (constant pressure) method find the following:
  Invert $T_o(t)$ as $t_o(T)$
  Find $1/R_o(T) = dt_o(T)/dT$
  $\omega_o(T) = (L_o/d_o)^2 \phi_o \eta_o(T)$ $$*p_{c,o} = \frac{3}{4} \cdot \frac{(p_{i,o} + p_{o,o})^2}{p_{i,o}^2 + p_{i,o}p_{o,o} + p_{o,o}^2} \cdot (p_{i,o} - p_{o,o})$$

$t_{M,o}(T) = \omega_o(T)/p_{c,o}$
For the translated (constant flow) method find the following:
  $\omega(T) = (L/d)^2 \phi \eta(T)$
  $\Omega(T) = \omega(T)/(\epsilon L)$ $$p_i = \sqrt{p_o^2 + 2p_{ref}\Omega JT/T_{ref}}$$

$$p_c = \frac{3}{4} \cdot \frac{(p_i + p_o)^2}{p_i^2 + p_i p_o + p_o^2} \cdot (p_i - p_o)$$

$t_M(T) = \omega(T)/p_c$ $$t(T) = \int_{T_{init}}^{T} \frac{t_M}{t_{M,o}} \cdot \frac{dT}{R_0(T)}$$

T(t) is an inversion of t(T)
*NOTE: Skip this step if $p_{c,o}$ (rather than $p_{i,o}$ and $p_{o,o}$) is a known
constant compressed pressure CALCULATION OF THE DURATION, $t_p$, OF A TEMPERATURE
PLATEAU IN A TRANSLATED METHOD CORRESPONDING TO A
$t_{p,o}$-LONG PLATEAU AT A TEMPERATURE, $T_p$,
IN THE ORIGINAL METHOD:
For the original (constant pressure) method find the following:
  $\omega_o = (L_o/d_o)^2 \phi_o \eta_o(T_p)$ $$*p_{c,o} = \frac{3}{4} \cdot \frac{(p_{i,o} + p_{o,o})^2}{p_{i,o}^2 + p_{i,o}p_{o,o} + p_{o,o}^2} \cdot (p_{i,o} - p_{o,o})$$

$t_{M,o} = \omega_o/p_{c,o}$
For the translated (constant flow) method find the following:
  $\omega = (L/d)^2 \phi \eta(T_p)$
  $\Omega = \omega/(\epsilon L)$ $$p_i = \sqrt{p_o^2 + 2p_{ref}\Omega JT/T_{ref}}$$

$$p_c = \frac{3}{4} \cdot \frac{(p_i + p_o)^2}{p_i^2 + p_i p_o + p_o^2} \cdot (p_i - p_o)$$

$t_M = \omega/p_c$
  $t_p = t_{p,o}(t_M/t_{M,o})$
  (this is the duration of a plateau at $T_p$ in a translated method)
*NOTE: Skip this step if $p_{c,o}$ (rather than $p_{i,o}$ and $p_{o,o}$) is a known
constant compressed pressure Mathematical solutions for the heating ramps become much simpler if column pressure drop in a translated method is very low ($|p_i - p_o| \ll p_o$) or very high ($p_i \gg p_o$)

Low pressure drop in a translated method, i.e. $|p_i - p_o| \ll p_o$
(Typically, this is the case for the capillary columns which have large
internal diameters)
MATHEMATICAL SOLUTION FOR A HEATING RAMP
STARTING AT $T_{init}$
For the original (constant pressure) method find the following:
  [repeat the same steps as in a general mathematical solution
  for a heating ramp as described above]
For the translated (constant flow) method find the following:
  $t_M(T) = \epsilon L p_o T_{ref}/(JT p_{ref})$ $$t(T) = \int_{T_{init}}^{T} \frac{t_M}{t_{M,o}} \cdot \frac{dT}{R_0(T)}$$

T(t) is an inversion of t(T)
Note: In many cases, an analytical solution for T(t) can be found. This
solution is especially simple in one practically important case when
original as well as translated methods utilize either helium, hydrogen, or
nitrogen as a carrier gas, and when the heating ramp, $R_o$, in the original
method is a fixed number. Under these conditions, gas viscosity,
$\eta(T)$, can be approximated as
  $\eta(T) = \eta_{init}(T/T_{init})^\xi$, $\xi \approx 0.7$
and the analytical solution for temperature program, T(t), is $$T(t) = \frac{T_{init}}{(1 - \xi G_{init} R_0 t)^{1/\xi}} \approx \frac{T_{init}}{(1 - 0.7 G_{init} R_0 t)^{1.43}}$$

where $$G_{init} = \frac{t_{M,o}(T_{init})}{t_M(T_{init})}$$

High pressure drop in a translated method, i.e. $p_i \gg p_o$
(Typically, this is the case for the capillary columns having a small
internal diameter or for packed columns operating with an outlet close to
ambient conditions, and for all columns operating with an outlet
at vacuum)

-continued

MATHEMATICAL SOLUTION FOR A HEATING RAMP
STARTING AT $T_{init}$
For the original (constant pressure) method find the following:
  [repeat the same steps as in the general mathematical solution
  as described above]
For the translated (constant flow) method find the following:

$$t_M = \sqrt{\frac{16L^3 \phi \varepsilon \eta(T)}{18d^2 p_{ref} JT/T_{ref}}}$$

$$t(T) = \int_{T_{init}}^{T} \frac{t_M}{t_{M,o}} \cdot \frac{dT}{R_0(T)}$$

T(t) is an inversion of t(T)
Note: Under these conditions described in the Note above
for a system having a low pressure drop, the analytical solution
for the temperature program, T(t), is
  $T(t) = T_{init}(1 + 0.5(1 - \xi)G_{init}R_o t)^{2/(1-\xi)} \approx T_{init}(1 + 0.15G_{init}R_o t)^{6.67}$ Generation of Elution Pattern for a Calibration Table The above techniques illustrate generating a second method to run on a GC system, based on a given first method. To derive information from the results of GC analysis using the second method, an elution pattern for a calibration table is generated. To illustrate such generation, a sequence of dimensionless elution times, $\tau_A$, $\tau_B$, $\tau_C$, etc., for a sequence of peaks A, B, C, etc., corresponding to the sequence of solutes A, B, C, etc. is an elution pattern for these solutes. This pattern is unique for all mutually translatable analyses of the same mixture, and can be included in a calibration table (for the peak identification) that can be also unique for all mutually translatable analyses of the same mixture.

In addition to or instead of the normalized elution times, a sequence of elution temperatures, $T_A$, $T_B$, $T_C$, etc. can be used as an elution pattern for the same solutes. This pattern is also unique for all mutually translatable analyses of the same mixture. Unfortunately, all solutes eluting during the temperature plateau have the same elution temperature, and, hence, can not be identified from the thermal elution pattern. To resolve the ambiguity, the thermal elution pattern for the peaks eluting during the same temperature plateau can be complimented by the pattern based on dimensionless times. In this case, it can be convenient to reset the counting of the dimensionless time at the beginning of each temperature plateau.

Use (t, τ)-table and/or (t, T)-table together with predetermined interpo-
lation rules to convert a sequence of peak retention times
into elution pattern.
If necessary for a visual peak identification, mark each peak in a
visually displayed chromatogram by its dimensionless elution time and/or
elution temperature (in addition to or instead of the traditionally used
retention time markers).

Elution Pattern Locking (EPL)

Method parameters of an actual analysis can be different from their nominal values. As a result, the departure of the actual elution pattern from the nominally expected one can exceed an acceptable tolerance. To make sure that the actual elution patter remains within the tolerance, actual values of critical parameters can be measured and the method can be translated to accommodate the actual values. This eliminates or substantially reduces the errors in the solute elution pattern. The critical parameters that effect the solute elution pattern are the ones that effect the void time, $t_M$, as a function of time, t, and temperature T.

On the highest level, void time, $t_M$, is calculated as $t_M = \omega/p_c$ where $p_c$ is compressed pressure drop and $\omega = \alpha \eta$, where $\alpha$ is a constant and $\eta$ is a temperature dependent gas viscosity.

To eliminate the errors in $\omega$, measure $t_M$ at a known $p_c$ and T, and calculate a correct value of $\alpha$ as:

$$\alpha = p_c t_M/\eta$$

The errors in $t_M$ can also come from errors in $p_c$. If $p_c$ is calculated from inlet pressure, $p_i$, and outlet pressure, $p_o$, then both might require a more accurate measurement or recalibration. Frequently, unless a special value of $p_o$ is known from the requirements of a detector (example: $p_o=0$ for mass spectrometers, $p_o$ should be about 0.1 bar above ambient pressure for some atomic emission detectors, etc.), its value is assumed to be the same as the ambient pressure, $p_a$, ignoring the detector pressure drop, $\Delta p_d$. For the columns (such as capillary columns with relatively large internal diameters) requiring a low column pressure drop, neglecting $\Delta P_d$ can be a source of substantial errors in the calculation of $p_c$.

To eliminate the errors in ω, measure $t_M$ at a known $p_c$ and T,
and calculate correct value of α as:
  $\alpha = p_c t_M/\eta$
For the reduction of errors in $p_c$, calibrate $\Delta p_d$ and count its effect on $p_o$
as
  $p_o = p_a + \Delta p_d$
before calculating $p_c$.
Use the most accurate values of ω and $p_c$ during the generation of
normalized temperature programs as well as during their execution.
Notes:
Execution of a given normalized temperature program along with more
accurate specific method parameters leads to a transparent EPL.
In case of a constant flow mode, changes in method parameters lead to
changes in (actual) temperature and pressure programs.

Visual Evaluation of Peak Alignment in Mutually Translatable Chromatograms

To visually align all peaks corresponding to the same solute in several chromatograms resulting from (possibly, very different mutually translatable methods) use dimensionless time as the time axes.

I claim:

1. A method for method translation from a first method for performing gas chromatographic analysis to a second method for performing gas chromatographic analysis in a gas chromatography system, the method comprising the steps of:

translating from a temperature program based on time in the first method to a normalized temperature program, the normalized temperature program based on a dimensionless time, τ, wherein $$\tau = \int_0^t dt/t_M$$

where $t_M$ is void time and wherein void time is the time for an unretained solute to travel through the gas chromatography system; and generating a temperature program for the second method based on the normalized temperature program and a set of pre-selected conditions for the second method.

2. A method for translation from an original method for performing a gas chromatographic analysis to a translated method for performing a gas chromatographic analysis where the translation is done in a way that a dimensionless retention time of any solute in a gas chromatographic analysis, hereinafter translated analysis, performed according to a translated method is the same as a dimensionless retention time of that solute in a gas chromatographic analysis, hereinafter original analysis, performed according to the original method; and where either the original method or the translated method or both methods can have a temperature program for changing a column temperature during a gas chromatographic analysis, and/or a pneumatic program for changing pneumatic parameters during a gas chromatographic analysis wherein a pneumatic parameter is a carrier gas flow rate or a carrier gas velocity or a column head pressure or a column outlet pressure or a compressed pressure drop or another parameter, other than column temperature, that affects a value of one or more of the above mentioned pneumatic parameters in a programmable way.

3. The method of claim 2 where a column temperature and/or one or two controlled pneumatic parameters in the original method or in the translated method or in both methods can be maintained at a constant level during the gas chromatographic analysis.

4. The method of claim 3 where a program is expressed as a collection of points wherein each point is a pair of time and parameter and where a predetermined algorithm is provided for the interpolation between the neighboring points.

5. The method of claim 3 comprising all or some of the following time transformation steps:
  (i) transformation of actual time of an original analysis into dimensionless time by means of a time transformation formula;
  (ii) constructing a time transformation table for the original method, the table consisting of a number of points, each point being a pair of actual time and dimensionless time, that is sufficient for reconstruction of a precise value of actual time corresponding to an arbitrary dimensionless time or for reconstruction of a precise value of dimensionless time corresponding to an arbitrary actual time;
  (iii) transformation of dimensionless time into actual time in a translated analysis by means of a time reconstruction formula; and
  (iv) constructing a time transformation table for translated method.

6. The method of claim 3 for translation of a temperature program and/or a pneumatic program in a gas chromatographic analysis where all time entries in an actual program are the actual times and all time entries in a normalized program are the dimensionless times, the method comprising all or some of the following steps:
  (i) translation of actual temperature program of the original method to a normalized temperature program where dimensionless time is either calculated by means of a time transformation formula or reconstructed from a time transformation table specified in the original method,
  (ii) translation of actual pneumatic program of the original method to a normalized pneumatic program where dimensionless time is either calculated via the use of the time transformation formula or reconstructed from the time transformation table specified in the original method,
  (iii) translation of normalized programs to those actual programs for the translated method that are necessary for the complete description of the translated method, and
  (iv) translation of actual programs in the original method to those actual programs in the translated method that are necessary for the complete description of the translated method.

7. The method of claim 3 that, in order to allow for the heating rate in a temperature program to be clamped by the maximal heating rate available during a particular gas chromatographic analysis, comprises the steps of:
  (i) changing the column temperature with the heating rate that is the highest available in a particular gas chromatographic instrument for a particular gas chromatographic analysis, but that is below the rate specified in the method for performing the gas chromatographic analysis; and
  (ii) compensating for the shortfall in the heating rate by means of an automatic adjustment in controlled pneumatic parameters calculated from method translation where the heating rate specified in the method for performing the gas chromatographic analysis is the original heating rate and the clamped heating rate is the translated heating rate.

8. A method of claim 3 that, in order to allow for the rate of change in a pneumatic parameter controlled by a pneumatic program to be clamped by the maximal rate available during a particular gas chromatographic analysis, comprises the steps of:
  (i) changing the pneumatic parameter with the rate that is the highest available in a particular gas chromatographic instrument for a particular gas chromatographic analysis, but that is below the rate specified in the method for performing the gas chromatographic analysis; and
  (ii) compensating for the shortfall in the rate of change of a pneumatic parameter during a heating ramp by means of an automatic adjustment in the heating rate calculated from method translation where the rate of change of the pneumatic parameter specified in the method for performing the gas chromatographic analysis is the original rate of change of that pneumatic parameter and the clamped rate of change is the translated rate.

9. The method of claim 3 for the translation of a calibration table for peak identification in a gas chromatographic analysis where all time entries in an actual calibration table are the actual times and all time entries in a normalized calibration table are the dimensionless times, the method comprising all or some of the following steps:
  (i) specifying a normalized calibration table of an original method as the normalized calibration table of a translated method,
  (ii) translating an actual calibration table of an original method and specifying it as the normalized calibration table of an original and/or of a translated method,
  (iii) translating the normalized calibration table into an actual calibration table for a translated method, and
  (iv) translating an actual calibration table of an original method into an actual calibration table for a translated method.

10. The method of claim 3 comprising all or some of the following steps:
  (i) input of known method parameters of the original and of the translated method for performing a gas chromatographic analyses, the list of parameters including but not limited to: column dimensions, type of a carrier gas, temperature programs, pneumatic programs, and so forth;
  (ii) input of required performance parameters for the translated analysis, the list of parameters including but not limited to: separation power or its change compared to the original analysis, analysis time or its change compared to the original analysis, sample capacity or its change compared to the original analysis, maximal temperature and its maximal rate of change, maximal pressure and its maximal rate of change, maximal flow and its maximal rate of change, and so forth;

(iii) input of optimization goals for the translated analysis, the optimization goals such as achieving the best separation power, achieving the shortest analysis time, achieving the best separation-speed tradeoff, and so forth;

(iv) translation of an original method into a translated method; and (v) output of parameters of the translated and of the original method for performing a gas chromatographic analysis, the list of parameters including but not limited to the lists in clauses (i), (ii) and (iii) of this claim.

11. The method of claim 3 that, in order for a manual and/or an automatic locking of the normalized calibration table in a root method for performing a gas chromatographic analyses, comprises all or some of the following steps:

(i) measurement of void time at a predetermined reference temperature and reference values of pneumatic parameters, (ii) updating a specification for column parameters in the root method so that the void time calculated from the specified column parameters is the same as the measured void time, (iii) performing a gas chromatographic analysis to generate a set of dimensionless retention times for the peaks of interest, and (iv) recording the dimensionless retention times in the normalized calibration table of the root method, hereinafter reference normalized calibration table, that is designated for peak identification in all translations and replications of the root method.

12. The method of claim 11 that, in order for a manual and/or an automatic locking a peak elution pattern in a routine gas chromatographic analyses performed according to a replication or a translation of a root method, comprises all or some of the following steps:

(i) measurement of void time at the predetermined reference temperature and reference values of a pneumatic parameters, (ii) calculation of the column parameters from the measured void time, (iii) method translation using the method for performing a gas chromatographic analysis with the specified column parameters as the original method and the method for performing a gas chromatographic analysis with the parameters calculated in step (ii) as the translated method, and (iv) using the method translated in step (iii) incorporating the reference normalized calibration table as the method for performing a locked chromatographic analyses and for identification of the peaks generated in that analysis.

13. The method of claim 3 that, in order for a manual and/or an automatic locking a peak elution pattern in a routine gas chromatographic analyses performed according to a replication or a translation of a root method, comprises all or some of the following steps:

(i) identifying a reference solute in a root gas chromatographic analysis performed according to a root method, (ii) specifying dimensionless retention time of the reference solute in a root gas chromatographic analysis as the reference dimensionless retention time of the solute, (iii) measuring dimensionless retention time of the reference solute in a routine gas chromatographic analysis, (iv) if difference between the measured and the reference dimensionless retention time of the reference solute is larger than acceptable value for that difference then changing specification for one or more column dimensions in the method for performing a routine gas chromatographic analysis in order to change its void time, (v) method translation using the method for performing a routine gas chromatographic analysis with the specified column parameters as the original method and the method changed in step (iv) as the translated method, and (vi) repeating steps (iii) through (v) in accordance with a suitable iteration algorithm until the difference between the measured and the reference dimensionless retention time of the reference solute is reduced to acceptable value.

14. The method of claim 3 that, in order for a manual and/or an automatic locking a peak elution pattern in a routine temperature programmed gas chromatographic analyses performed according to a replication or a translation of a root method, comprises all or some of the following steps:

(i) identifying a reference solute eluting during a heating ramp in a root gas chromatographic analysis performed according to a root method, (ii) specifying elution temperature of the reference solute in a root gas chromatographic analysis as the reference elution temperature of the solute, (iii) measuring elution temperature of the reference solute in a routine gas chromatographic analysis, (iv) if difference between the measured and the reference elution temperature of the reference solute is larger than acceptable value for that difference then changing specification for one or more column dimensions in the method for performing a routine gas chromatographic analysis in order to change its void time, (v) method translation using the method for performing a routine gas chromatographic analysis with the specified column parameters as the original method and the method changed in step (iv) as the translated method, and (vi) repeating steps (iii) through (v) in accordance with a suitable iteration algorithm until the difference between the measured and the reference elution temperature of the reference solute is reduced to acceptable value.

15. The method of claim 3 that, in order for a manual and/or an automatic optimization of a separation of a target peak pair at a constant value of a controlled pneumatic parameter, comprises all or some of the following steps:

(i) setting the pneumatic parameter to the value prescribed by the method for performing the gas chromatographic analysis, (ii) changing the value of the pneumatic parameter, (iii) translating the method for performing the gas chromatographic analysis to accommodate the change in the pneumatic parameter, (iv) performing the translated gas chromatographic analysis, (v) measuring a quality of separation of the target peak pair as the resolution of the pair or as other metric of quality of separation known in gas chromatography, and (vi) repeating steps (ii) through (v) in accordance with a suitable iteration algorithm until a required or the best possible quality of separation of the target peak pair is achieved.

16. The method of claim 15 that, in order for a manual and/or an automatic optimization of separation of two or more target peak pairs, comprises all or some of the following steps:

(i) optimization of separation of the earliest eluting peak pair, (ii) selecting the next earliest eluting peak pair from the list of the target peak pairs to be optimized, (iii) choosing a new set value of the pneumatic parameter and the set time when the set value has to be in effect, (iv) changing the pneumatic program to perform a programmable change of the pneumatic parameter in order to achieve the set value of the parameter at the set time, (v) translating the method for performing the gas chromatographic analysis to accommodate the change in the pneumatic program, (vi) performing the translated gas chromatographic analysis, (vii) measuring the quality of separation of the selected peak pair, (viii) repeating steps (iii) through (vii) in accordance with a suitable iteration algorithm until a required or the best possible quality of separation of the selected peak pair is achieved, and (ix) repeating steps (ii) through (viii) until the separation of all target peak pairs is optimized.

* * * * *